(12) United States Patent
Min et al.

(10) Patent No.: US 10,617,779 B2
(45) Date of Patent: Apr. 14, 2020

(54) VACUUM EXHAUST SYSTEM OF STERILIZER

(71) Applicant: CMTECH CO., LTD., Dong-gu (KR)

(72) Inventors: Heung Sik Min, Dong-gu (KR); Young Keun Ahn, Dalseo-gu (KR); Sung Jin Yang, Dalseo-gu (KR); Jin Woo Min, Dong-gu (KR)

(73) Assignee: CMTECH CO. LTD., Daegu (KR)

( * ) Notice: Subject to any disclaimer, the term of this patent is extended or adjusted under 35 U.S.C. 154(b) by 0 days.

(21) Appl. No.: 16/258,105

(22) Filed: Jan. 25, 2019

(65) Prior Publication Data
US 2019/0151489 A1    May 23, 2019

Related U.S. Application Data

(62) Division of application No. 15/124,223, filed as application No. PCT/KR2015/006353 on Jun. 23, 2015, now Pat. No. 10,232,073.

(30) Foreign Application Priority Data

Jun. 27, 2014    (KR) .......................... 10-2014-0079925

(51) Int. Cl.
*A61L 2/20* (2006.01)
*A61L 2/26* (2006.01)
(Continued)

(52) U.S. Cl.
CPC .............. *A61L 2/208* (2013.01); *A61L 2/206* (2013.01); *A61L 2/26* (2013.01); *F04B 37/14* (2013.01);
(Continued)

(58) Field of Classification Search
CPC . A61L 2/208; A61L 2/26; A61L 2/206; A61L 2202/24; A61L 2202/122;
(Continued)

(56) References Cited

U.S. PATENT DOCUMENTS 3,948,601 A * 4/1976 Fraser ....................... A61L 2/14
422/23
4,583,301 A * 4/1986 Crowley ................... F26B 5/04
34/177
(Continued)

FOREIGN PATENT DOCUMENTS

CN          203060357 U    7/2013
JP          1995-077184 A  3/1995
(Continued)

OTHER PUBLICATIONS

International Search Report issued in corresponding International Application No. PCT/KR2015/006353 dated Aug. 19, 2015, 5 pages.

*Primary Examiner* — Regina M Yoo
(74) *Attorney, Agent, or Firm* — Snyder, Clark, Lesch & Chung, LLP

(57) ABSTRACT

The invention relates to a vacuum exhaust system of a sterilizer, comprising: a sterilization chamber; a first vacuum pump connected to one side of the sterilization chamber; an oil mist trap section for exhausting steam incoming from the sterilization chamber via the first vacuum pump; and a second vacuum pump connected to the first vacuum pump and the oil mist trap section. The vacuum exhaust system of a sterilizer according to the invention comprises the second vacuum pump connected to the first vacuum pump and the oil mist trap section, wherein by turning the second vacuum pump on to apply a vacuum to the operating oil in the first vacuum pump, thereby providing a certain pressure for evaporating water in liquid state to the first vacuum pump, the invention can vaporize the water vapor trapped in the operating oil in the first vacuum pump.

4 Claims, 7 Drawing Sheets

(51) Int. Cl.
    *F04B 39/16*         (2006.01)
    *F04B 41/06*         (2006.01)
    *F04B 37/14*         (2006.01)

(52) U.S. Cl.
    CPC .............. *F04B 39/16* (2013.01); *F04B 41/06* (2013.01); *A61L 2202/122* (2013.01); *A61L 2202/24* (2013.01)

(58) Field of Classification Search
    CPC .. A61L 2/20; F04B 37/14; F04B 41/06; F04B 39/16
    See application file for complete search history.

(56) References Cited

U.S. PATENT DOCUMENTS

| | | |
|---|---|---|
| 4,690,097 A | 9/1987 | Fukuta et al. |
| 6,609,411 B1 | 8/2003 | Taylor et al. |
| 7,892,486 B2 | 2/2011 | Mizuno et al. |
| 2002/0063087 A1 | 5/2002 | Spearman et al. |

FOREIGN PATENT DOCUMENTS

| | | |
|---|---|---|
| JP | 2008-200511 A | 9/2008 |
| KR | 10-2007-0037880 A | 4/2007 |
| KR | 10-0751490 B1 | 8/2007 |
| KR | 10-1348222 B1 | 1/2014 |

\* cited by examiner

[Fig. 1]
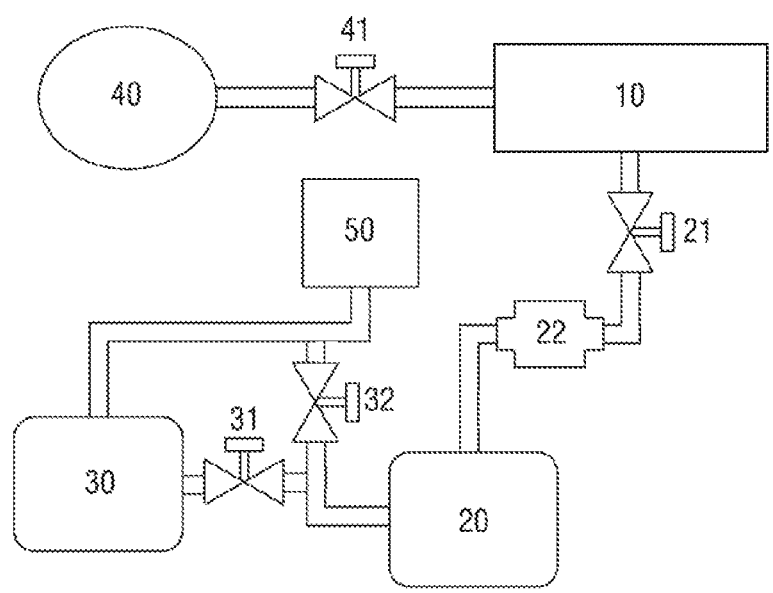

[Fig. 2]
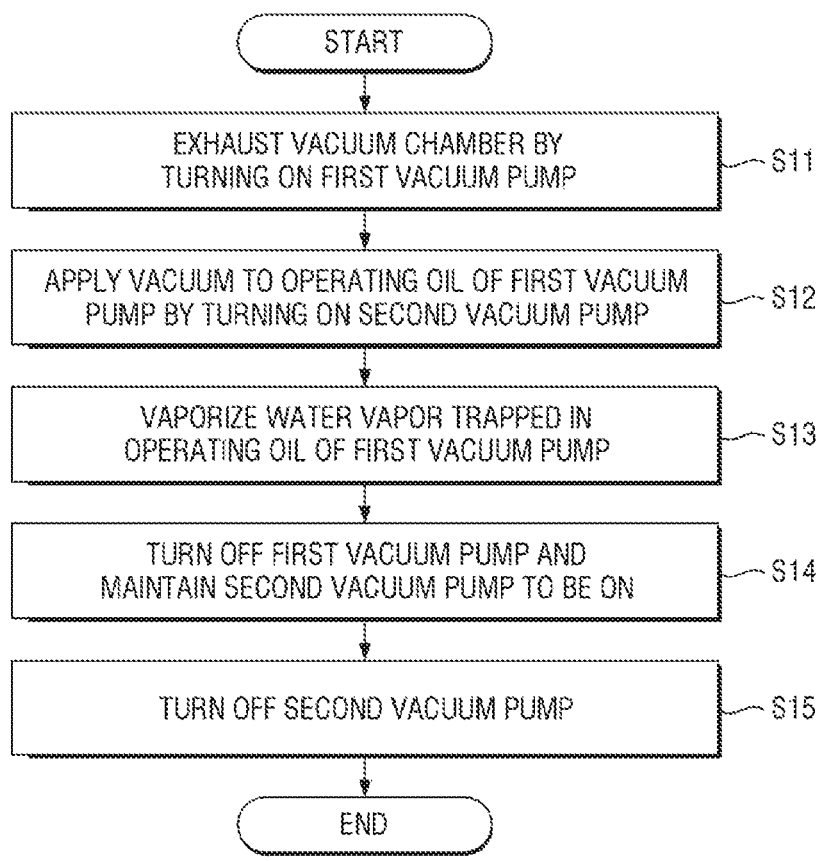

[Fig. 3]
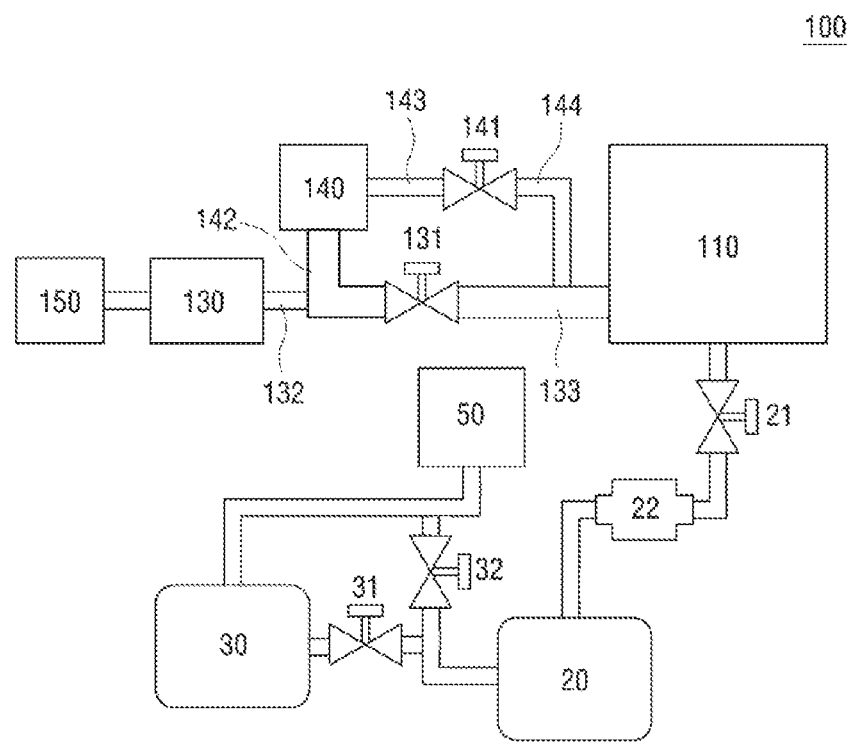

[Fig. 4]
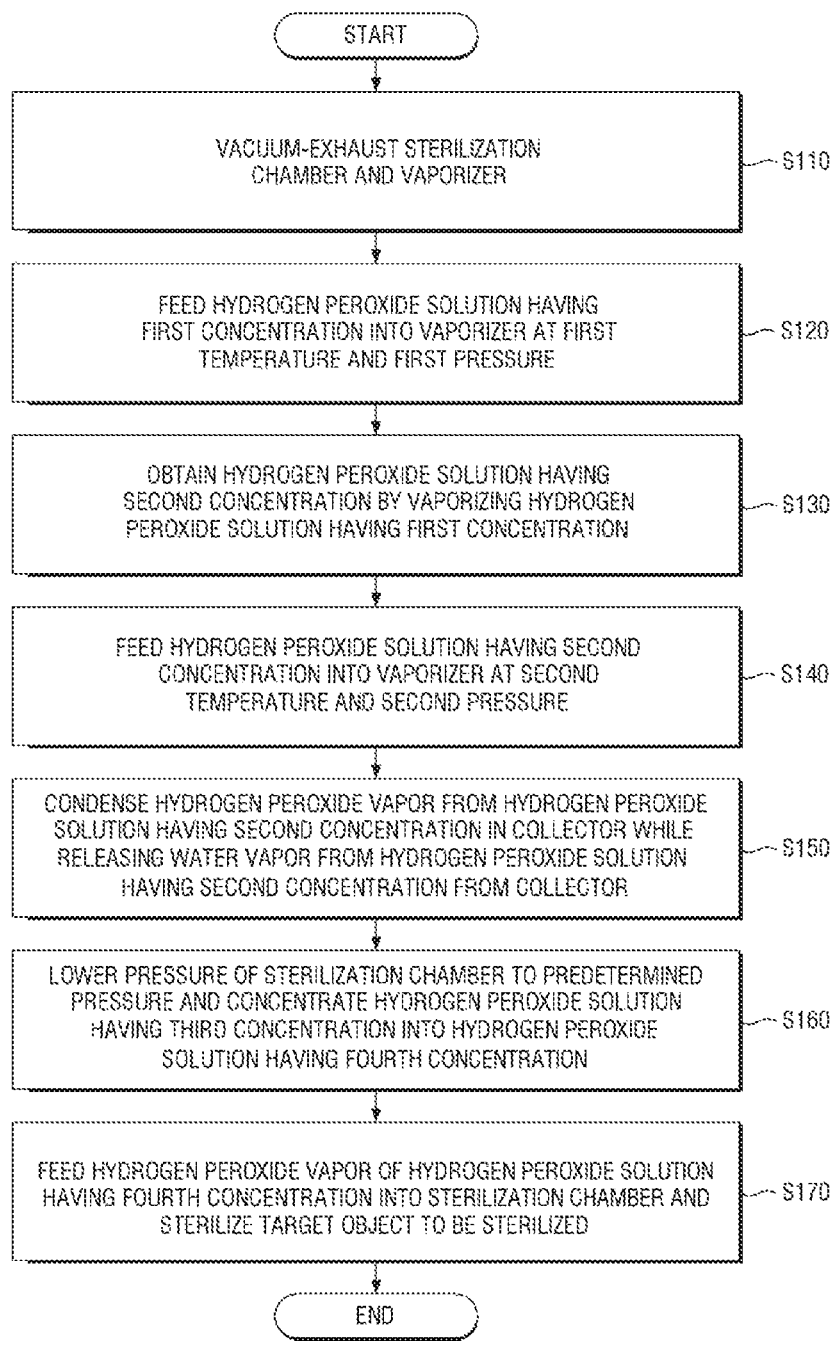

[Fig. 5]
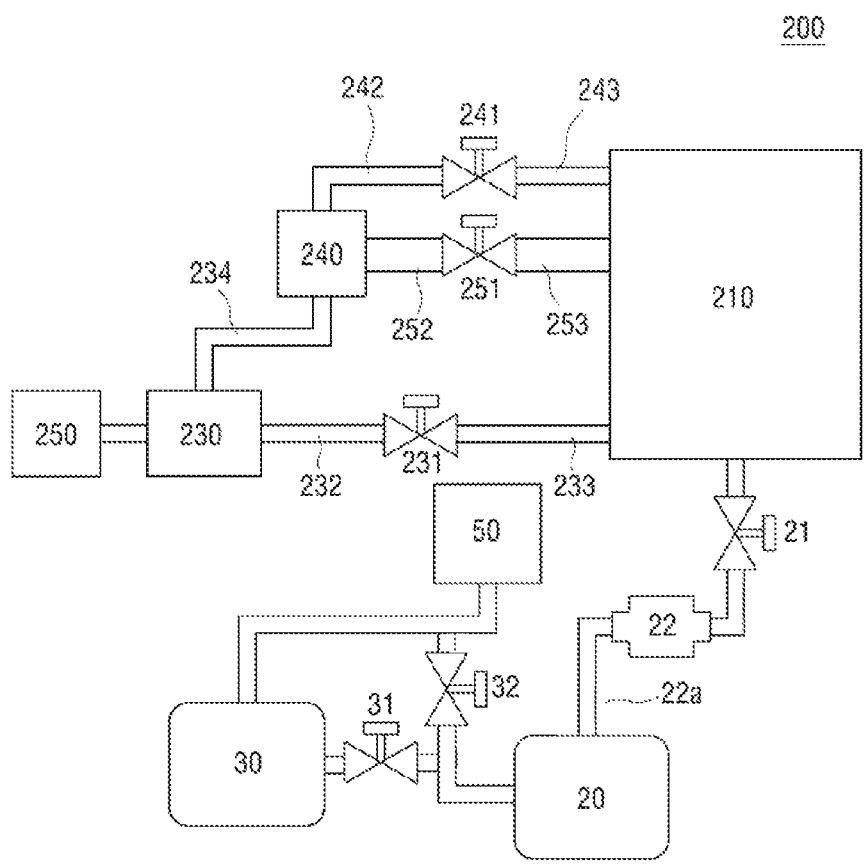

[Fig. 6]
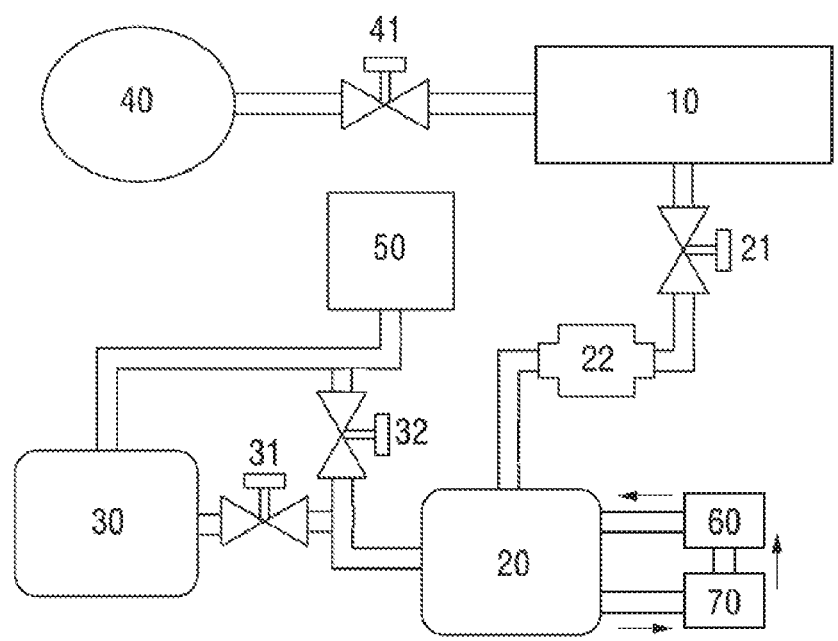

[Fig. 7]
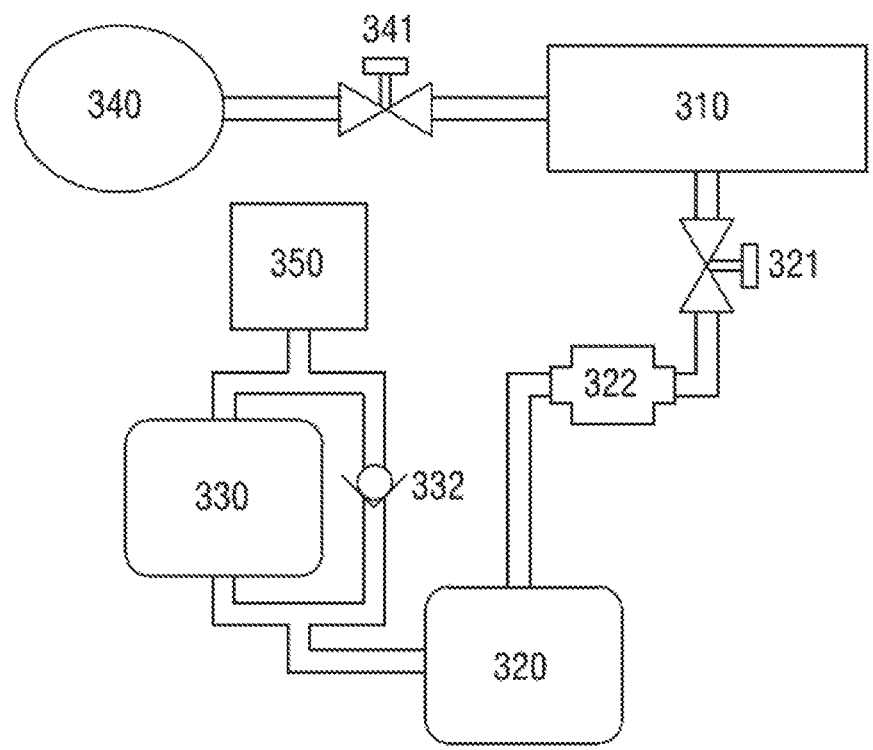

VACUUM EXHAUST SYSTEM OF STERILIZER

CROSS-REFERENCE TO RELATED APPLICATIONS

This application is a divisional of U.S. application Ser. No. 15/124,223 filed on Sep. 7, 2016, which claims the benefit of International Application No. PCT/KR2015/006353, filed on Jun. 23, 2015, which claims priority to Korean Application No. 10-2014-0079925 filed on Jun. 27, 2014. All of these applications are incorporated by reference herein.

TECHNICAL FIELD

The invention relates to a vacuum exhaust system of a sterilizer, and more particularly, a vacuum exhaust system of a sterilizer for preventing moisture from being trapped in a vacuum pump oil.

BACKGROUND ART

Medical instruments and devices are routinely sterilized by a high-pressure vapor sterilization method using water vapor saturated under a high pressure or by an ethylene oxide gas sterilization method using a chemical material such as ethylene oxide that does not cause thermal damage to tools or materials susceptible to heat.

More specifically, a high-pressure vapor sterilizer or an autoclave performs sterilization at a high temperature of about 120° C. or higher and may thus shorten the life of medical instruments and devices by causing deformation of medical appliances formed of a synthetic resin and blunting the sharp edges of medical appliances formed of steel. Particularly, expensive medical instruments and devices that are on the increase due to recent developments in surgical technology are generally susceptible to heat or moisture and are highly likely to be damaged during sterilization reprocessing. Thus, the high-pressure vapor sterilization method may not be a suitable option for such expensive medical instruments and devices.

An ethylene oxide gas sterilizer capable of minimizing thermal damage to medical instruments or devices can perform sterilization at low temperature, but requires a ventilation time of more than 12 hours after sterilization because of the possibility of any remaining ethylene oxide gas or the reaction products thereof causing carcinogenic or toxic substances. Also, the use of an ethylene oxide gas requires great care because an ethylene oxide gas is highly explosive, has been reported to serve as a genetic toxic substance causing mutations, and has even been known as a carcinogenic substance.

A sterilization method using hydrogen peroxide vapor boasts of various advantages, for example, a short sterilization time of about 30 to 60 minutes at a temperature of 40 to 50° C. and the release of harmless sterilization by-products to the human body or the environment, such as water and oxygen, and can address the shortcomings of a high-pressure vapor sterilizer and an ethylene oxide gas sterilizer.

The sterilization method using hydrogen peroxide vapor inevitably produces water vapor, and the water vapor passes through a vacuum pump while being released.

Some of the water vapor either continues to evaporate or is dissolved and released into the air. However, the water vapor cannot be completely discharged, and some of the water vapor may be trapped and accumulated in the oil of the vacuum pump.

Also, in a case in which a sterilization cycle involves the removal of moisture from a sterilant solution, the rate of accumulation moisture in the oil of the vacuum pump increases.

In this case, if too much water vapor is accumulated in the oil of the vacuum pump in the form of moisture, the water vapor may corrode the inner surfaces of the vacuum pump or deteriorate the vacuum exhaust performance.

Also, if too much moisture is contained in the oil of the vacuum pump, moisture cannot be sufficiently trapped by an oil mist trap section and the like while being released, thereby imposing a spatial restriction on the space where the equipment can be used.

Also, not only water vapor evaporated from a hydrogen peroxide solution, but also water vapor from a sterilization target washed and not sufficiently dried or having moisture adsorbed thereon, accelerates the trapping and accumulation of moisture in the vacuum pump.

However, the performance of a dry vacuum pump not using an oil is relatively poorer than the performance of an oil vacuum pump. Also, an expensive dry vacuum pump with high vacuum exhaust performance may not be suitable for vacuum-exhausting a container with a large volume due to its insufficient throughput.

DISCLOSURE

Technical Problems

To address the aforementioned problems, exemplary embodiments of the invention provide a vacuum exhaust system of a sterilizer for preventing moisture from being trapped in a vacuum pump oil.

Additional advantages, subjects, and features of the invention will be set forth in part in the description which follows and in part will become apparent to those having ordinary skill in the art upon examination of the following or may be learned from practice of the invention.

Technical Solutions

According to an aspect of the invention, a vacuum exhaust system of a sterilizer includes: a sterilization chamber; a first vacuum pump connected to one side of the sterilization chamber; an oil mist trap section for releasing vapor introduced from the sterilization chamber via the first vacuum pump; and a second vacuum connected to the first vacuum pump and the oil mist trap section.

The vacuum exhaust system may further include a sterilant solution feeding device connected to the other side of the sterilization chamber.

The first vacuum pump may be an oil vacuum pump.

The second vacuum pump may be a dry vacuum pump not using an oil.

The second vacuum pump may expose an operating oil of the first vacuum pump to a vacuum level with a predetermined pressure, and the predetermined pressure may be a pressure at which moisture trapped in the operating oil of the first vacuum pump can reach a point below its boiling point.

The vacuum exhaust system may further include a first path opening/closing valve section provided between the first vacuum pump and the oil mist trap section, and the second vacuum pump and the first path opening/closing valve section may be connected in parallel between the first vacuum pump and the oil mist trap section.

The first path opening/closing valve section may be a check valve

According to another aspect of the invention, a vacuum exhaust method of a sterilizer includes: exhausting a vacuum chamber by turning on a first vacuum pump; applying a vacuum to an operating oil of the first vacuum pump by turning on a second vacuum pump; and vaporizing water vapor trapped in the operating oil of the first vacuum pump.

The vacuum exhaust method may further include, after the vaporizing the water vapor, turning off the first vacuum pump and maintaining the second vacuum pump to be turned on; and turning off the second vacuum pump.

The vacuum exhaust method may further include, after the vaporizing the water vapor, turning off the second vacuum pump.

The vacuum exhaust method may further include, after the exhausting the vacuum chamber, terminating the exhaust of the vacuum chamber by turning off the first vacuum pump.

Advantageous Effects

According to exemplary embodiments of the invention, the second vacuum pump connected to the first vacuum pump and the oil mist trap section is provided. By turning on the second vacuum pump, a vacuum can be applied to the operating oil of the first vacuum pump, and as a result, a predetermined pressure for vaporizing water in a liquid state in the first vacuum pump can be provided. Therefore, water vapor trapped in the operating oil of the first vacuum pump can be vaporized.

BRIEF DESCRIPTION OF DRAWINGS

FIG. 1 is a schematic perspective view of a vacuum exhaust system of a sterilizer according to a first exemplary embodiment of the present disclosure.

FIG. 2 is a flowchart illustrating a vacuum exhaust method of the vacuum exhaust system of the sterilizer according to the first exemplary embodiment.

FIG. 3 is a schematic view of a first application example of the vacuum exhaust system of the sterilizer according to the first exemplary embodiment.

FIG. 4 is a flowchart illustrating a sterilization method of the first application example of the vacuum exhaust system of the sterilizer according to the first exemplary embodiment.

FIG. 5 is a schematic view of a second application example of the vacuum exhaust system of the sterilizer according to the first exemplary embodiment.

FIG. 6 is a schematic perspective view of a vacuum exhaust system of a sterilizer according to a second exemplary embodiment of the present disclosure.

FIG. 7 is a schematic view of a vacuum exhaust system of a sterilizer according to a third exemplary embodiment of the present disclosure.

BEST MODES FOR CARRYING OUT THE INVENTION

Advantages and features of the invention and methods of accomplishing the same may be understood more readily by reference to the following detailed description of exemplary embodiments and the accompanying drawings. The invention may, however, be embodied in many different provides and should not be construed as being limited to the embodiments set forth herein. Rather, these embodiments are provided so that this disclosure will be thorough and complete and will fully convey the concept of the invention to those skilled in the art, and the invention will only be defined by the appended claims.

Like reference numerals refer to like elements throughout the specification. Furthermore, in the present disclosure, the expression "and/or" includes any and all combinations of the associated listed words.

In the present disclosure, expressions including ordinal numbers, such as "first" and "second," etc., may modify various elements. However, such elements are not limited by the above expressions. For example, the above expressions do not limit the sequence and/or importance of the elements. The above expressions are used merely for the purpose to distinguish an element from the other elements. For example, a first user device and a second user device indicate different user devices although both of them are user devices. For example, a first element could be termed a second element, and similarly, a second element could be also termed a first element without departing from the scope of the present disclosure.

It will be further understood that the terms "comprises" and/or "comprising," or "includes" and/or "including" when used in this specification, specify the presence of stated features, regions, integers, steps, operations, elements, and/or components, but do not preclude the presence or addition of one or more other features, regions, integers, steps, operations, elements, components, and/or groups thereof.

Unless otherwise defined, all terms (including technical and scientific terms) used herein have the same meaning as commonly understood by one of ordinary skill in the art to which this invention belongs. It will be further understood that terms, such as those defined in commonly used dictionaries, should be interpreted as having a meaning that is consistent with their meaning in the context of the relevant art and/or the specification and will not be interpreted in an idealized or overly formal sense unless expressly so defined herein.

Spatially relative terms, such as "beneath", "below", "lower", "under", "above", "upper" and the like, may be used herein for ease of description to describe one element or feature's relationship to another element(s) or feature(s) as illustrated in the figures. It will be understood that the spatially relative terms are intended to encompass different orientations of the device in use or operation in addition to the orientation depicted in the figures. In an exemplary embodiment, when the device in the figures is turned over, elements described as "below" or "beneath" or "under" other elements or features would then be oriented "above" the other elements or features. Thus, the exemplary terms "below" and "under" can encompass both an orientation of above and below.

Exemplary embodiments of the invention will hereinafter be described with reference to the accompanying drawings.

FIG. 1 is a schematic perspective view of a vacuum exhaust system of a sterilizer, according to a first exemplary embodiment of the present disclosure.

Referring to FIG. 1, the vacuum exhaust system of the sterilizer according to the first exemplary embodiment includes a sterilization chamber 10.

The sterilization chamber 10 is a container capable of receiving a target object to be sterilized such as a medical instrument or a surgical tool. The sterilization chamber 10 may have a door at one side thereof, through which the target object can be put in or out of the sterilization chamber 10.

A sterilant solution feeding device 40, which is connected to one side of the sterilization chamber 10, may be provided, and the target object can be sterilized in the sterilization chamber 10 with a sterilant fed from the sterilant solution feeding device 40.

A sterilant solution feeding control valve 41 may be provided between the sterilant solution feeding device 40 and the sterilization chamber 10 and may thus be able to feed an appropriate amount of sterilant solution.

The sterilant may be hydrogen peroxide, and the sterilant solution may be a hydrogen peroxide solution.

A first vacuum pump 20, which is connected to the other side of the sterilization chamber 10, may be provided. The first vacuum pump 20 may create a vacuum by pumping the gas out of the sterilization chamber 10.

The first vacuum pump 20 may be an oil vacuum pump. More specifically, a dry vacuum pump not using an oil generally has poorer vacuum exhaust performance than an oil vacuum pump. Also, an expensive dry vacuum pump with high vacuum exhaust performance may not be suitable for vacuum-exhausting a container with a large volume due to its insufficient throughput. Thus, the first vacuum pump 20 may preferably be an oil vacuum pump.

A first vacuum valve 21, which is capable of controlling the operation of the first vacuum pump 20, may be connected between the sterilization chamber 10 and the first vacuum pump 20.

A catalyst reaction section 22 may be provided between the sterilization chamber 10 and the first vacuum pump 20.

Vapor released from the sterilization chamber 10 and introduced into the first vacuum pump 20 may contain toxic ingredients. The catalyst reaction section 22 oxidize the toxic ingredients, thereby producing a harmless exhaust gas.

However, the invention is not limited to the presence or absence of the catalyst reaction section 22.

Referring further to FIG. 1 the vacuum exhaust system of the sterilizer according to the first exemplary embodiment may also include an oil mist trap section 50.

The oil mist trap section 50 is a part for trapping an oil from vapor introduced from the sterilization chamber 10 and released via the first vacuum pump 20. An oil may be trapped by the oil mist trap section 50, and vapor may be discharged through the oil mist trap section 50.

The first vacuum pump 20 and the oil mist trap section 50 may be elements commonly used in a typical sterilizer.

A sterilization method using a sterilant solution generally produces water vapor, and the water vapor passes through a vacuum pump while being released.

Some of the water vapor either continues to evaporate or is dissolved and discharged into the air. However, the water vapor cannot be completely discharged. Thus, some of the water vapor is trapped and accumulated in the oil of the vacuum pump.

Also, in a case in which a sterilization cycle involves the removal of moisture from a sterilant solution, the rate at which moisture is accumulated in the oil of the first vacuum pump increases.

In this case, if water vapor continues to be accumulated too much in the oil of the first vacuum pump in the form of moisture, the water vapor may corrode the inner surfaces of the first vacuum pump or deteriorate first vacuum exhaust performance.

Also, if too much moisture is contained in the oil of the first vacuum pump, moisture cannot be sufficiently trapped by the oil mist trap section 50 while being released. Thus, since equipment needs to be installed in the space where oil mist is allowed, a spatial restriction on the space where the equipment can be used arises.

Thus, a second vacuum pump may be provided to prevent water vapor from being trapped and accumulated in the oil of the first vacuum pump in a case in which an oil vacuum pump is used as the first vacuum pump.

More specifically, referring to FIG. 1, the vacuum exhaust system of the sterilizer according to the first exemplary embodiment includes a second vacuum pump 30, which is connected to the first vacuum pump 20 and the oil mist trap section 50.

The second vacuum pump 30 is a dry vacuum pump not using an oil. If the second vacuum pump is an oil vacuum pump, water vapor may undesirably be trapped and accumulated in the oil of the second vacuum pump. Thus, the second vacuum pump 30 may preferably be a dry vacuum pump not using an oil.

The second vacuum pump 30 is configured to expose an operating oil of the first vacuum pump 20 to a vacuum level with a predetermined pressure, and the predetermined pressure may be a pressure at which moisture trapped in the operating oil can reach a point below its boiling point.

That is, as mentioned above, some of water vapor passing through the first vacuum pump either continues to evaporate or is dissolved and released into the air. However, the water vapor cannot be completely discharged, and some of the water vapor is trapped and accumulated in the oil of the vacuum pump.

Thus, to evaporate water in a liquid state trapped in the oil of the first vacuum pump, a predetermined vacuum level for evaporating the water in a liquid state in the first vacuum pump 20 may be provided, and the second vacuum pump 30 may provide the predetermined vacuum level for evaporating the water trapped in the first vacuum pump 20.

As mentioned above, the predetermined pressure may be a pressure at which moisture trapped in the operating oil can reach a point below its boiling point. More specifically, the predetermined pressure may be 50 to 150 mb.

Accordingly, the second vacuum pump 30 may be a dry vacuum pump capable of providing a pressure of 50 to 150 mb.

It will hereinafter be described how the second vacuum pump 30 is connected to the first vacuum pump 20 and the oil mist trap section 50.

Referring to FIG. 1, the second vacuum pump 30 may be connected in series to the first vacuum pump 20 and the oil mist trap section 50.

A first path opening/closing valve section 31 is provided between the second vacuum pump 30 and the first vacuum pump 20, and water vapor introduced from the first vacuum pump 20 may pass through the second vacuum pump 30 via the first path opening/closing valve section 31 and may finally pass through the oil mist trap section 50.

A second path opening/closing valve section 32 is provided between the first vacuum pump 20 and the oil mist trap section 50, and the water vapor introduced from the first vacuum pump 20 may pass through the oil mist trap section 50 either via the second vacuum pump 30 or without passing through the second vacuum pump 30.

That is, the water vapor introduced from the first vacuum pump 20 may or may not pass through the second vacuum pump 30 depending on whether the first path opening/closing valve section 31 and the second path opening/closing valve section 32 are open or closed.

FIG. 1 illustrates an example in which two valve sections, i.e., the first path opening/closing valve section 31 and the second path opening/closing valve section 32, are used.

Alternatively, the turning on or off of first and second paths may be controlled using a single check valve, which will be described later in detail with reference to a third exemplary embodiment of the present disclosure.

A vacuum exhaust method of the vacuum exhaust system of the sterilizer according to the first exemplary embodiment will hereinafter be described.

FIG. 2 is a flowchart illustrating a vacuum exhaust method of the vacuum exhaust system of the sterilizer according to the first exemplary embodiment.

Referring to FIG. 2, the vacuum exhaust method of the vacuum exhaust system of the sterilizer according to the first exemplary embodiment includes vacuum-exhausting the vacuum chamber by turning on the first vacuum pump (S11).

As will be described later, the first vacuum pump may be repeatedly turned on or off, and a state in which the first vacuum pump is on may correspond to the step of vacuum-exhausting the vacuum chamber.

In this case, a vacuum level in an exhaust section of the first vacuum pump may be atmospheric pressure or higher, and a vacuum level in the sterilization chamber may be 10 to 150 mb.

In S11, the first vacuum valve 21 may be open, the first path opening/closing valve section 31 may be closed, and the second path opening/closing valve section 32 may be open.

Thereafter, by turning on the second vacuum pump, a vacuum may be applied to the operating oil of the first vacuum pump (S12).

As mentioned above, some of water vapor passing through the first vacuum pump either continues to evaporate or is dissolved and released into the air. However, the water vapor cannot be completely discharged, and some of the water vapor may be trapped and accumulated in the oil of the vacuum pump in the form of a liquid.

Thus, according to the invention, a predetermined pressure may be provided to allow the water in a liquid state in the oil of the first vacuum pump 20 to evaporate, and the second vacuum pump 30 may provide a predetermined pressure for vaporizing the water in a liquid state trapped in the oil of the first vacuum pump 20.

In this case, the vacuum level in the exhaust section of the first vacuum pump may be atmospheric pressure to 50 mb, and the vacuum level in the sterilization chamber may be 10 to 150 mb.

In S12, the first vacuum valve 21 may be open, the first path opening/closing valve section 31 may be open, and the second path opening/closing valve section 32 may be closed.

In the step of applying a vacuum to the operating oil of the first vacuum pump by turning on the second vacuum pump, i.e., S12, the first vacuum pump may be on or off.

That is, a vacuum may be applied to the operating oil of the first vacuum pump by turning on the second vacuum pump in S12 when the first vacuum pump is on, i.e., while the vacuum chamber is being vacuum-exhausted via the first vacuum pump.

Also, a vacuum may be applied to the operating oil of the first vacuum pump by turning on the second vacuum pump in S12 when the first vacuum pump is off, i.e., when the vacuum-exhausting of the vacuum chamber via the first vacuum pump is complete.

Thus, according to the invention, the step of terminating the vacuum-exhausting of the vacuum chamber by turning off the first vacuum pump may be further performed after the step of vacuum-exhausting the vacuum chamber by turning on the first vacuum pump, i.e., S11.

That is, after the step of terminating the vacuum-exhausting of the vacuum chamber by turning off the first vacuum pump, the second vacuum pump may be turned on so as to apply a vacuum to the operating oil of the first vacuum pump.

Thereafter, water vapor trapped in the operating oil of the first vacuum pump is vaporized (S13).

S12 and S13 may be performed at the same time. That is, the predetermined pressure for vaporizing the water in a liquid state in the first vacuum pump may be provided to the first vacuum pump by turning on the second vacuum pump so as to apply a vacuum to the operating oil of the first vacuum pump, and as a result, water vapor trapped in the operating oil of the first vacuum pump may be vaporized.

In other words, since the water vapor trapped in the operating oil of the first vacuum pump is vaporized, the water in a liquid state can be released via the oil mist trap section 50 without being trapped in the operating oil.

In this case, the vacuum level in the exhaust section of the first vacuum pump may be 50 to 150 mb, and the vacuum level in the sterilization chamber may be 0.1 to 20 mb.

In S13, the first vacuum valve 21 may be open, the first path opening/closing valve section 31 may be open, and the second path opening/closing valve section 32 may be closed.

Thereafter, the first vacuum pump is turned off, and the second vacuum pump is maintained to be turned on (S14).

That is, in S14, the first vacuum pump may be turned off to terminate the vacuum-exhausting of the sterilization chamber, but the water in a liquid state trapped in the operating oil of the first vacuum pump may continue to be vaporized.

In this case, the vacuum level in the exhaust section of the first vacuum pump may be 50 to 150 mb, and the vacuum level in the sterilization chamber may be 0.5 to 1 mb.

In S14, the first vacuum valve 21 may be closed, the first path opening/closing valve section 31 may be open, and the second path opening/closing valve section 32 may be closed.

S14 may not be performed if the vacuum exhaust time is sufficiently long and the rate at which a gas containing water vapor is released from the chamber is low.

However, if the vacuum exhaust time is short and the exhaust speed of the second vacuum pump is low, S14 may be additionally performed. That is, S14 is not necessarily essential.

Thereafter, by turning off the second vacuum pump, the vacuum exhaust process of the vacuum exhaust system of the sterilizer according to the first exemplary embodiment is completed.

As mentioned above, the second vacuum pump 30, which is connected to the first vacuum pump 20 and the oil mist trap section 50, is provided, and by turning on the second vacuum pump 30, a vacuum is applied to the operating oil of the first vacuum pump. Accordingly, the predetermined pressure for vaporizing the water in a liquid state in the first vacuum pump 20 can be provided, and as a result, water vapor trapped in the operating oil of the first vacuum pump can be vaporized.

An application example of the vacuum exhaust system of the sterilizer according to the first exemplary embodiment will hereinafter be described.

FIG. 3 is a schematic view of a first application example of the vacuum exhaust system of the sterilizer according to the first exemplary embodiment.

The vacuum exhaust system of the sterilizer according to the first exemplary embodiment is as already described above, and thus, a detailed description thereof will be omitted. A sterilizer in accordance with a first application example will hereinafter be described.

Referring to FIG. 3, a first application example 100 of a vacuum exhaust system of a sterilizer according to a first exemplary embodiment of the present disclosure includes a sterilization chamber 110.

The sterilization chamber 110 may be a vessel for receiving a target object to be sterilized, such as a medical instrument or a surgical instrument. The sterilization chamber 110 may include a door, which is provided at one side of the sterilization chamber 110 and through which the target enters or exits the sterilization chamber 110.

The sterilization chamber 110 may also include a first vacuum pump 20, which is connected to one side of the sterilization chamber 110, and the first vacuum pump 20 may create a vacuum by pumping the gas out of the sterilization chamber 110. A first vacuum valve 21 capable of controlling an operation of the first vacuum pump 20 is connected between the sterilization chamber 110 and the first vacuum pump 20. The sterilization chamber 110 is as already described above, and thus, a detailed description thereof will be omitted.

Referring further to FIG. 3, the first application example 100 also includes a vaporizer 130 (also referred to as an evaporator), which is connected to the other side of the sterilization chamber 110 and supplies a hydrogen peroxide vapor to the sterilization chamber 110, and a hydrogen peroxide supply device 150, which supplies hydrogen peroxide to the vaporizer 130.

A vaporization valve 131 may be provided between the sterilization chamber 110 and the vaporizer 130.

The first application example 100 also includes a collector 140 (also referred to as a collecting vaporizer), which has one side connected to the vaporizer 130 and the other side connected to the sterilization chamber 110 and concentrates the hydrogen peroxide supplied to the vaporizer 130.

The vaporization valve 131 may be provided between the sterilization chamber 110 and the collector 140.

A collection valve 141 may also be provided between the sterilization chamber 110 and the collector 140.

That is, the vaporization valve 131 and the collection valve 141 may be connected in parallel between the sterilization chamber 110 and the collector 140.

As described above, the vaporization valve 131 may be provided between the sterilization chamber 110 and the vaporizer 130. That is, the vaporization valve 131 may have one side connected to the sterilization chamber 110 and the other side connected in parallel between the vaporizer 130 and the collector 140.

Referring further to FIG. 3, the first application example 100 also includes a first connecting pipe 142, which connects the collector 140 and the vaporization valve 131 and a second connecting pipe 133, which connects the vaporization valve 131 and the sterilization chamber 110.

The sterilization apparatus 100 using a hydrogen peroxide solution, according to the first exemplary embodiment, may also include a third connecting pipe 143, which connects the collector 140 and the collection valve 141, and a fourth connecting pipe 144, which connects the collection valve 141 and the sterilization chamber 110.

FIGS. 1A and 1B illustrate the fourth connecting pipe 144 as being connected to the second connecting pipe 133 so as for the vaporization valve 131 and the collection valve 141 to be connected in parallel between the sterilization chamber 110 and the collector 140, but the invention is not limited thereto. That is, alternatively, the fourth connecting pipe 144 may be connected directly to the sterilization chamber 110 so as for the vaporization valve 131 and the collection valve 141 to be connected in parallel between the sterilization chamber 110 and the collector 140.

The sterilization apparatus 100 using hydrogen peroxide may also include a fifth connecting pipe 132, which connects the vaporizer 130 and the vaporization valve 131. FIGS. 1A and 1B illustrate the fifth connecting pipe 132 as being connected to the first connecting pipe 142 so as for the vaporization valve 131 to be connected in parallel to the vaporizer 130 and the collector 140, but the invention is not limited thereto. That is, alternatively, the fifth connecting pipe 132 may be connected directly to the vaporization valve 131 so as for the vaporization valve 131 to be connected in parallel between the vaporizer 130 and the collector 140.

The vaporization valve 131 and the collection valve 141 may control the flow of a fluid in each of the first, second, third, fourth, and fifth connecting pipes 142, 133, 143, 144, and 132 through an "open/close" operation. The "open/close" operation for the vaporization valve 131 and the collection valve 141 may be controlled by an additional controller.

The first connecting pipe 142, which connects the collector 140 and the vaporization valve 131, and the second connecting pipe 133, which connects the vaporization valve 131 and the sterilization chamber 110, may have a larger inner diameter than the other connecting pipes. For example, in response to the third, fourth, and fifth connecting pipes 143, 144, and 132 being ¼-inch pipes, the first and second connecting pipes 142 and 133 may be 1-inch pipes, and this will be described later in detail.

Although not specifically illustrated, temperature control means for controlling the temperature of the sterilization chamber 110, the vaporizer 130, and the collector 140 may be provided. The temperature control means may be a heater, which is obvious to a person skilled in the art to which the invention pertains, and thus, a detailed description of the temperature control means will be omitted.

The collector 140 may include cooling means as temperature control means thereof. The cooling means may use an appraise cooling method such as a direct cooling method using a coolant or a thermoelectric device or an air cooling method using a heat exchanger.

A sterilization method using the first application example will hereinafter be described.

FIG. 4 is a flowchart illustrating a sterilization method of the first application example.

Referring to FIG. 4, the sterilization method of the first application example includes vacuum-exhausting the sterilization chamber 110 (also referred to as a pasteurization chamber) and the vaporizer 130 (S110).

The sterilization chamber 110 and the vaporizer 130 may be vacuum-exhausted by turning on the first vacuum pump 20 and opening the first vacuum valve 21.

S110, i.e., a step of vacuum-exhausting the sterilization chamber and the vaporizer, may be continued until S160, which will be described later, begins, and may be completed in response to the sterilization chamber 110 reaching a predetermined pressure and a hydrogen peroxide liquid with moisture removed therefrom being trapped in the collector.

To vacuum-exhaust the vaporizer 130, the vaporization valve 131 between the sterilization chamber 110 and the vaporizer 130 or the collection valve 141 between the sterilization chamber 110 and the collector 140 may be opened to be in communication with the sterilization chamber currently being vacuum-exhausted and thus to lower the pressure below atmospheric pressure, and may be closed in a subsequent step.

During the vacuum-exhausting of the sterilization chamber 110 and the vaporizer 130, the sterilization chamber and the vaporizer may be maintained at a predetermined temperature by the aforementioned temperature control means.

Thereafter, the sterilization method according to the present exemplary embodiment includes introducing a hydrogen peroxide solution having a first concentration into the vaporizer 130 at a first temperature and a first pressure (S120).

The introduction of the hydrogen peroxide solution may be performed by the hydrogen peroxide supply device 150, which stores the hydrogen peroxide solution. Although not specifically illustrated in FIG. 3, a hydrogen peroxide supply control valve (not illustrated) may be provided between the vaporizer 130 and the hydrogen peroxide supply device 150, and thus, an appropriate amount of the hydrogen peroxide solution may be supplied.

The first concentration may be 60 wt % or less.

In reality, the concentration of a hydrogen peroxide solution that can be handled is generally limited to 60 wt % or lower, and thus, it is difficult to use a hydrogen peroxide solution with a concentration of higher than 60 wt % as a sterilant.

That is, the first concentration is the concentration of a hydrogen peroxide solution that can be handled, and is not necessarily of great significance in understanding the subject matter of the invention.

The first temperature may range from 60° C. to 70° C., and the first pressure may be 800 mb or atmospheric pressure.

In S120, while the hydrogen peroxide solution having the first concentration is being introduced into the vaporizer 130, the vaporization valve 131 and the collection valve 141 may be closed, or may remain open depending on the type of the hydrogen peroxide supply device.

In S120, the sterilization chamber 110 may have a pressure of 800 mb to atmospheric pressure and a temperature of 38° C. to 42° C.

The first temperature may be higher than the temperature of the sterilization chamber.

The first temperature may correspond to the temperature of the vaporizer at which more water vapor can be vaporized from the hydrogen peroxide solution. During the vaporization of water vapor, a very strong endothermic reaction occurs, strongly suppressing the rate of vaporization.

To enhance the rate of vaporization, the pressure of the vaporizer may be lowered so as to increase the degree of vacuum, in which case, the vaporization rate of hydrogen peroxide may also increase, resulting in an increase in the consumption of hydrogen peroxide. Also, sufficient energy for vaporizing the hydrogen peroxide solution may not be properly provided at low temperature. Thus, the first temperature may be set to be higher than at least the temperature of the sterilization chamber.

Thereafter, the sterilization method according to the present exemplary embodiment includes obtaining a hydrogen peroxide solution having a second solution by vaporizing the hydrogen peroxide solution having the first concentration (S130).

That is, in response to the hydrogen peroxide solution having the first concentration being vaporized in the vaporizer 130 (i.e., water being removed from the hydrogen peroxide solution), the hydrogen peroxide solution having the second concentration is obtained.

The second concentration may be 75 wt % to 85 wt %. Accordingly, S130 may be a primary hydrogen peroxide solution concentration step for obtaining a hydrogen peroxide solution having a concentration of 75 wt % to 85 wt % by vaporizing a hydrogen peroxide solution having a concentration of 60 wt % or less.

In general, water evaporates more quickly than hydrogen peroxide at a given temperature and pressure because the vapor pressure of water is higher than the vapor pressure of hydrogen peroxide. Also, since the molecular weight of water is lower than the molecular weight of hydrogen peroxide, water diffuses more quickly than hydrogen peroxide.

Since water (or moisture) evaporates and diffuses more quickly than hydrogen peroxide at a given temperature and pressure, the water in a hydrogen peroxide solution also evaporates and diffuses into the air more quickly than the hydrogen peroxide in the hydrogen peroxide solution. Thus, the hydrogen peroxide solution having the second concentration may be obtained.

In S130, evaporated water may be vacuum-exhausted by the first vacuum pump through the sterilization chamber 110. Thus, in S130, the first vacuum pump 20 may be turned on, and the first vacuum valve 21 and the vaporization valve 131 may be opened.

In S130, due to an endothermic reaction during the vaporization of the hydrogen peroxide solution having the first concentration through the first vacuum pump, the temperature of the vaporizer 130 may temporarily decrease and may thus be in the range of 55° C. to 65° C., and the vaporizer 130 may have a pressure of 30 mb to 800 mb.

While evaporated water is being vacuum-exhausted by the vacuum pump through the sterilization chamber 110, the sterilization chamber 110 may have a pressure of 10 mb to 600 mb and a temperature of 45° C. to 55° C., and the collector 140 may have a pressure of 20 mb to 500 mb and a temperature of 35° C. to 40° C.

As S130 proceeds, the throughput of the first vacuum pump decreases once the vacuum level in the chamber reaches 10 mb to 150 mb. However, in S130, the ratio of water vapor passing through the vacuum pump rapidly increases, and the rate at which water vapor accumulates in the oil of the vacuum pump increases.

In S130, a vacuum exhaust process of the aforementioned vacuum exhaust system may begin.

That is, S130 may be a step that requires the removal of moisture contained in the oil of the vacuum pump in accordance with a sterilization process. Thus, in S130, like in S12, the step of applying a vacuum to the operating oil of the first vacuum pump by turning on the second vacuum pump, may be performed.

However, the beginning of S12 is not necessarily limited to S130, and S140 through S160 that will be described later may be set as the beginning of S12 as necessary.

Thereafter, the sterilization method according to the present exemplary embodiment includes injecting the hydrogen peroxide solution having the second concentration into the collector at a second temperature and a second pressure (S140).

To feed the hydrogen peroxide solution having the second concentration into the collector 140 at the second temperature and the second pressure, the first vacuum pump 20 may be turned on, the first vacuum valve 21 may be opened, the vaporization valve 131 may be closed, and the collection valve 141 may be turned on.

The second temperature may be 35° C. to 42° C., and the second pressure may be 8 mb to 50 mb.

While the hydrogen peroxide solution having the second concentration is being transferred from the vaporizer 130 to the collector 140, the vaporizer 130 may have a pressure of 10 mb to 60 mb and a temperature of 55° C. to 60° C. The hydrogen peroxide solution having the second concentration may be transferred from the vaporizer 130 to the collector 140 via the second connecting pipe 132 and the first connecting pipe 142.

Even in S140, the vacuum-exhausting of the sterilization chamber 110 is continued so that the sterilization chamber 110 may have a pressure of 1 mb to 10 mb and a temperature of 45° C. to 55° C.

The second temperature may be lower than the temperature of the sterilization chamber.

The second temperature may correspond to the temperature of the collector during the collection of the hydrogen peroxide solution having the second concentration. In response to the temperature of a hydrogen peroxide vapor saturated from the vaporizer being higher than the temperature of the sterilization chamber, the hydrogen peroxide vapor may be released through the sterilization chamber, instead of being condensed in the collector.

Even if some of the hydrogen peroxide vapor is condensed at early stages of S140 and S150, the condensed hydrogen peroxide may easily evaporate again and thus may not remain in the collector as long as the temperature of the collector is higher than the temperature of the sterilization chamber, because the vaporization heat of hydrogen peroxide is lower than the vaporization heat of water vapor. As a result, S170 may not be able to be performed. Thus, the second temperature may be lower than at least the temperature of the sterilization chamber.

As mentioned above, S134, i.e., the step of obtaining the hydrogen peroxide solution having the second concentration by vaporizing the hydrogen peroxide solution having the first concentration, may be performed, and then S140, i.e., a step of injecting the hydrogen peroxide solution having the second concentration into the collector at the second temperature and the second pressure, may be performed.

Instead, a method in which S140 is performed without performing S130, i.e., the hydrogen peroxide solution having the first concentration is directly injected into the collector, may be taken into consideration. This method may be inappropriate for the reasons that will be explained below.

Table 1 shows the vaporization rate of hydrogen peroxide vapor in various hydrogen peroxide solutions having different solutions.

That is, performing S140 without performing S130 may mean injecting a hydrogen peroxide solution having a concentration of, for example, 60 wt %, into the collector, and performing S130 and then S140 may mean injecting a hydrogen peroxide solution having a concentration of 80 wt % into the collector.

In the case of performing S140 without performing S130, the ratio of water vapor passing through the collector at an early stage of S140 may be relatively high, compared to the case of performing S130 and then S140.

If a hydrogen peroxide solution with a high ratio of water vapor to hydrogen peroxide vapor is injected into the collector, the water vapor may be condensed in the collector because of a high pressure in the collector (for example, a pressure higher than a saturated water vapor pressure of 75 mb when the temperature of the collector is 40° C.).

If the water vapor is condensed in the collector, there is a limit in the degree to which a hydrogen peroxide solution can be concentrated due to the condensed water vapor.

In the present exemplary embodiment, to prevent water vapor from being condensed first in the collector to limit the degree to which a hydrogen peroxide solution can be concentrated, S130, i.e., the step of obtaining the hydrogen peroxide solution having the second concentration by vaporizing the hydrogen peroxide solution having the first concentration, may be performed first, and then S140, i.e., the step of injecting the hydrogen peroxide solution having the second concentration into the collector at the second temperature and the second pressure, may be performed.

Thereafter, the sterilization method according to the present exemplary embodiment includes condensing hydrogen peroxide vapor from the hydrogen peroxide solution having the second concentration in the collector, and releasing water vapor from the hydrogen peroxide solution having the second concentration from the collector (S150).

As already mentioned above, water evaporates more quickly than hydrogen peroxide at a given temperature and pressure because the vapor pressure of water is higher than the vapor pressure of hydrogen peroxide. Also, since the molecular weight of water is lower than the molecular weight of hydrogen peroxide, water diffuses into the air more quickly than hydrogen peroxide. Since water (or moisture) evaporates and diffuses more quickly than hydro-

TABLE 1

| | HP wt % | | | | | | | | | | |
|---|---|---|---|---|---|---|---|---|---|---|---|
| Temperature | 50% | 55% | 60% | 65% | 70% | 75% | 80% | 83% | 85% | 90% | 95% |
| 50° C. | 8% | 10% | 13% | 17% | 23% | 31% | 40% | 47% | 52% | 66% | 82% |
| 60° C. | 9% | 11% | 14% | 19% | 25% | 32% | 42% | 48% | 53% | 67% | 83% |
| 70° C. | 9% | 12% | 15% | 20% | 26% | 34% | 43% | 50% | 55% | 68% | 84% |

Referring to Table 1, the higher the concentration of a hydrogen peroxide solution and the higher the temperature, the higher the vaporization rate of hydrogen peroxide vapor relative to the vaporization rate of water vapor.

For example, at a temperature of 50° C., the vaporization rate of hydrogen peroxide vapor is 13% in a hydrogen peroxide solution having a concentration of 60 wt %, which means that the rest of the hydrogen peroxide solution, i.e., 87% of the hydrogen peroxide solution, is water vapor, and the vaporization rate of hydrogen peroxide vapor is 40% in a hydrogen peroxide solution having a concentration of 80 wt %, which means that the rest of the hydrogen peroxide solution, i.e., 60% of the hydrogen peroxide solution, is water vapor.

gen peroxide at a given temperature and pressure, the water in a hydrogen peroxide solution also evaporates and diffuses into the air more quickly than the hydrogen peroxide in the hydrogen peroxide solution. Thus, hydrogen peroxide vapor is condensed in the collector, and water vapor is released from the collector. As a result, a hydrogen peroxide solution having a third concentration may be obtained.

That is, water has a higher vapor pressure than hydrogen peroxide, and thus, hydrogen peroxide vapor is condensed more easily than water vapor. Accordingly, a hydrogen peroxide solution condensed in the collector may contain a higher concentration of hydrogen peroxide than the hydrogen peroxide solution having the second concentration.

In S140, hydrogen peroxide vapor and water vapor may sequentially pass through the fifth connecting pipe, the first connecting pipe, the third connecting pipe, and the fourth connecting pipe, and the temperature of one or more small-inner diameter connecting pipes among the first, third, fourth, and fifth connecting pipes needs to be higher than the temperature of the collector 140.

More specifically, if the temperature of a connecting pipe to or from the collector is lower than the temperature of the collector, hydrogen peroxide vapor may remain condensed in the connecting pipe. Hydrogen peroxide vapor condensed in a connecting pipe with a small inner diameter may be exposed to a high temperature in S170, and thus, the content of water vapor may undesirably increase due to the decomposition of hydrogen peroxide at the stage of entering the sterilization chamber.

As shown in Table 1, once the concentration of a hydrogen peroxide solution is as high as, for example, less than 85 wt %, the ratios of water and hydrogen peroxide in the hydrogen peroxide solution are similar to each other, and the concentration of the hydrogen peroxide solution by a water/hydrogen peroxide vaporization ratio lowers the efficiency of concentration of the hydrogen peroxide solution.

At a given pressure, the temperature at which hydrogen peroxide vapor is condensed differs from the temperature at which water vapor is condensed. For example, at a temperature of 35° C., hydrogen peroxide is condensed at a pressure of 5 mb or higher, and water vapor is condensed at a pressure of 55 mb or higher.

Accordingly, when the temperature of the collector is 35° C. during the vacuum-exhausting of the collector via the collection valve, hydrogen peroxide vapor may be condensed, and water vapor may be released from the collector if the pressure of the collector is in the range of 5 mb to 55 mb.

The third concentration may be 90 wt % to 95 wt %. Accordingly, S150 may be a secondary hydrogen peroxide solution concentration step for obtaining a hydrogen peroxide solution having a concentration of 90 wt % to 95 wt % by vaporizing a hydrogen peroxide solution having a concentration of 75 wt % to 85 wt %.

In the present exemplary embodiment, S140, i.e., the step of injecting the hydrogen peroxide solution having the second concentration into the collector at the second temperature and the second pressure, and S150 i.e., a step of condensing hydrogen peroxide vapor from the hydrogen peroxide solution having the second concentration while releasing water vapor from the hydrogen peroxide solution having the second concentration from the collector, may be sequentially performed, but the invention is not limited thereto. That is, alternatively, S140 and S150 may be performed at the same time.

In other words, the hydrogen peroxide solution having the second concentration may be injected into the collector at the second temperature and the second pressure, and at the same time, hydrogen peroxide vapor from the hydrogen peroxide solution having the second concentration may be condensed while releasing water vapor from the hydrogen peroxide solution having the second concentration from the collector.

In S150, evaporated water may be vacuum-exhausted by the first vacuum pump. Thus, in S150, the first vacuum pump 20 may be turned on, and the first vaporization valve 21 may be opened so as to vacuum-exhaust evaporated water. Also, to vacuum-exhaust evaporated water through the first vacuum pump, the collection valve 141 may be opened.

Thereafter, the sterilization method according to the present exemplary embodiment includes lowering the pressure of the sterilization chamber to a predetermined pressure and obtaining a hydrogen peroxide solution having a fourth concentration by concentrating the hydrogen peroxide solution having the third concentration (S160).

The predetermined pressure may be a pressure for sterilizing a target object in the sterilization chamber. In response to the sterilant being hydrogen peroxide vapor, a vacuum state for facilitating the diffusion of hydrogen peroxide vapor needs to be established.

Thus, the predetermined pressure may be 0.5 mb to 1.3 mb, and the temperature of the sterilization chamber 110 may be 45° C. to 55° C.

The fourth concentration may be 95 wt % or higher. Accordingly, S160 may be a tertiary hydrogen peroxide solution concentration step for obtaining a hydrogen peroxide solution having a concentration of 95 wt % or higher by vaporizing a hydrogen peroxide solution having a concentration of 90 wt % to 95 wt %.

In S160, evaporated water may be vacuum-exhausted by the first vacuum pump. Thus, in S160, the first vacuum pump 20 may be turned on, and the first vacuum valve 21 may be opened so as to vacuum-exhaust evaporated water.

In S160, the collection valve 141 may be repeatedly opened and closed.

As the hydrogen peroxide solution having the third concentration is concentrated into the hydrogen peroxide solution having the fourth concentration, i.e., as the concentration of a hydrogen peroxide solution increases, the pressure at which hydrogen peroxide can be vaporized decreases.

At a given temperature of, for example, 45° C., hydrogen peroxide in a hydrogen peroxide solution having a concentration of 80 wt % is vaporized at a pressure of about 20 mb or lower, but hydrogen peroxide in a hydrogen peroxide solution having a concentration of 90 wt % is vaporized only at a pressure of about 11 mb or lower.

During the concentration of the hydrogen peroxide solution having the third concentration into the hydrogen peroxide solution having the fourth concentration, not only water, but also hydrogen peroxide, evaporates, thereby making it difficult to concentrate a hydrogen peroxide solution to more than a particular level.

That is, the decomposition of a high concentration of hydrogen peroxide may be continued, and moisture generated during the decomposition of the hydrogen peroxide may lower the concentration of the hydrogen peroxide.

To remove a small amount of such impurities as moisture, the pressure may be repeatedly increased and lowered within the range of 0.1 mb to 2 mb, in which case, moisture may be effectively removed while suppressing the vaporization of hydrogen peroxide.

This type of moisture removal may take time when the concentration of a hydrogen peroxide solution is low, but may be effective for the removal of a small amount of moisture from a hydrogen peroxide solution having a high concentration and at least for the maintenance of the high concentration of the hydrogen peroxide solution.

Due to the lowering of the pressure of the sterilization chamber to the predetermined pressure, the pressure of the collector 140 containing the hydrogen peroxide solution having the third concentration may continue to decrease, and as a result, hydrogen peroxide may be easily vaporized at a low pressure. To address this problem, the collection valve 141 may be repeatedly opened and closed, thereby preventing the pressure of the collector 140 from continuously decreasing.

In S160, the collector 140 may have a pressure of 5 mb to 10 mb and a temperature of 35° C., to 40° C., and the vaporizer 130 may have a pressure of 7 mb to 10 mb and a temperature of 60° C. to 70° C.

In S160, the hydrogen peroxide solution in the vaporizer is completely consumed, and thus, the temperature of the vaporizer is recovered in a vacuum state. A high concentration of hydrogen peroxide is trapped in the collector while a small amount of moisture is being removed therefrom, or stays in the collector while being maintained at a predetermined pressure.

In S160, the temperature of the collector may be further lowered by the temperature control means to prevent an excessive consumption of hydrogen peroxide.

Thereafter, the sterilization method according to the present exemplary embodiment includes injecting hydrogen peroxide vapor of the hydrogen peroxide solution having the fourth concentration into the sterilization chamber and sterilizing the target object in the sterilization chamber (S170).

In S170, to inject the hydrogen peroxide vapor of the hydrogen peroxide solution having the fourth concentration from the collector 140 into the sterilization chamber 110, the vaporization valve 131 may be opened, and the collection valve may be opened or closed.

That is, hydrogen peroxide may be transferred from the collector 140 to the sterilization chamber 110 via the first and second connecting pipes 142 and 133.

As already mentioned above, the first connecting pipe 142, which connects the collector 140 and the vaporization valve 131, and the second connecting pipe 133, which connects the vaporization valve 131 and the sterilization chamber 110, may have a larger inner diameter than the other connecting pipes, i.e., the third, fourth, and fifth connecting pipes 143, 144, and 132. For example, in response to the third, fourth, and fifth connecting pipes 143, 144, and 132 being ¼-inch pipes, the first and second connecting pipes 142 and 133 may be 1-inch pipes.

This is for preventing hydrogen peroxide vapor from infiltrating into the fifth connecting pipe 132 while being transferred into the sterilization chamber 110 via the first and second connecting pipes 142 and 133, and hydrogen peroxide vapor may not be introduced into the first connecting pipe 142, which has a relatively large inner diameter, but not into the fifth connecting pipe 132, which has a relatively small inner diameter.

In the present exemplary embodiment, hydrogen peroxide vapor not having a high temperature may be injected into the sterilization chamber to sterilize the target object.

If hydrogen peroxide vapor, which is vaporized in the collector when yet to be sufficiently saturated, enters the sterilization chamber while having a higher temperature than the sterilization chamber, the density of the hydrogen peroxide vapor may become excessively high in the path to the sterilization chamber, and thus, the hydrogen peroxide vapor may be easily condensed. As a result, the absolute amount of hydrogen peroxide that can be diffused into the sterilization chamber in a gaseous state may decrease, and a diffusion effect for sterilization may be adversely affected.

In the present exemplary embodiment, pipes in the path between the collector 140 and the sterilization chamber 110 may have a larger inner diameter than other pipes. The larger the inner diameter of a pipe, the larger the amount of gas that can be transferred via the pipe. Thus, a pipe having a large inner diameter may considerably increase the vaporization driving force resulting from the degree of vacuum by as much as the amount of gas that can be transferred via the pipe, and may thus prevent the temperature of hydrogen peroxide vapor from increasing.

That is, the less the amount of hydrogen peroxide vapor, the longer the amount of time that the hydrogen peroxide vapor is stayed in the collector and the higher the rate of decomposition of the hydrogen peroxide vapor in the collector that requires an increase in the temperature for the vaporization and the transportation of hydrogen peroxide. Thus, the concentrations of water vapor and an oxygen gas, which are the by-products of the decomposition of the hydrogen peroxide solution, increase. This, however, contradicts the purpose of minimizing the amount of water vapor, which interferes with the diffusion of hydrogen peroxide, as performed in the previous step, and may weaken the sterilization performance.

Thus, in the present exemplary embodiment, pipes having a large inner diameter may be provided in the path between the collector 140 and the sterilization chamber 110, and hydrogen peroxide vapor may be injected into the sterilization chamber when not having a high temperature. Accordingly, the decomposition of hydrogen peroxide by temperature may be minimized, hydrogen peroxide may be sufficiently diffused in a gaseous state, and the access of hydrogen peroxide vapor to the target object may be facilitated. As a result, an excellent sterilization effect may be achieved.

In response to the hydrogen peroxide solution having the fourth concentration being injected into the sterilization chamber 110, hydrogen peroxide may be diffused into the sterilization chamber in a gaseous state, and the heating rate of the collector 140 may be controlled such that the vaporization of the hydrogen peroxide may be almost complete before the temperature of the collector 140 reaches the temperature of the sterilization chamber.

That is, to promote the vaporization of hydrogen peroxide, the collector 140 may be heated by the temperature control means, and the heating rate of the collector may be controlled such that the vaporization of the hydrogen peroxide is at least 80% complete before the temperature of the collector reaches the temperature of the sterilization chamber.

In S170, the sterilization chamber 110 may have a pressure of 0.5 mb to 15 mb and a temperature of 45° C. to 55° C.

Also, the collector 140 have a pressure of 0.5 mb to 15 mb and a temperature of 30° C. to 70° C., and the vaporizer 130 may have a pressure of 0.5 mb to 15 mb and a temperature of 60° C. to 70° C. or higher.

In S170, S14 or S15, among other steps of the aforementioned vacuum exhaust method, may be performed.

The pressure and temperature conditions in each of the steps of the sterilization method according to the present exemplary embodiment are as shown in Table 2 below.

TABLE 2

| Classification | Vaporizer | | Collector | | Sterilization chamber | |
|---|---|---|---|---|---|---|
| | Pressure (mb) | Temperature (° C.) | Pressure (mb) | Temperature (° C.) | Pressure (mb) | Temperature (° C.) |
| S120 | 800~Atmospheric Pressure | 60~70 | 800~Atmospheric Pressure | 38~42 | 600~Atmospheric Pressure | 45~55 |
| S130 | 30~800 | 55~65 | 20~500 | 35~40 | 10~600 | 45~55 |
| S140, S150 | 10~60 | 55~60 | 8~50 | 35~42 | 1~10 | 45~55 |
| S160 | 7~10 | 60~70 | 5~10 | 35~40 | 0.5~1.3 | 45~55 |
| S170 | 0.5~15 | 60~70 | 0.5~15 | 30~70 | 0.5~15 | 45~55 |

The states of the first vacuum pump and the valves in each of the steps of the sterilization method according to the present exemplary embodiment are as shown in Table 3 below.

TABLE 3

| Classification | Vacuum Pump | Vacuum Valve | Vaporization Valve | Collection Valve |
|---|---|---|---|---|
| S120 | On or off | Open or Close | Close | Close |
| S130 | On | Open | Open | Open or close |
| S140, S150 | On | Open | Close | Open |
| S160 | On | Open | Close | Repeatedly open and close |
| S170 | Off | Close | Open | Open or close |

As described above, a highly-concentrated hydrogen peroxide solution may preferably be used to improve the sterilization performance. In reality, the concentration of a hydrogen peroxide solution that can be handled is generally limited to 60 wt % or lower, and thus, it is difficult to use a hydrogen peroxide solution with a concentration of higher than 60 wt % as a sterilant.

On the other hand, in the present exemplary embodiment, a hydrogen peroxide solution having a concentration of 95 wt % or higher may be obtained through multiple concentration steps and may be used as a sterilant. Also, water vapor's interference with diffusion may be reduced, and as a result, a sterilization effect may be considerably improved.

Also, by performing S140 and S150 after S130, i.e., the step of obtaining the hydrogen peroxide solution having the second concentration by removing moisture from the hydrogen peroxide solution having the first concentration, the probability of moisture being in contact with the collector may be reduced.

Also, by lowering the saturated vapor pressure of moisture according to the pressure and temperature of the collector, i.e., the "vaporization/condensation boundary pressure" of a hydrogen peroxide solution when injecting the hydrogen peroxide solution into the collector, a condition may be established in which moisture can be prevented from condensing even in contact with the collector.

As mentioned above, it is not necessarily true that the removal of moisture from a hydrogen peroxide solution during a vacuum process so as to increase the ratio of hydrogen peroxide vapor and thus to improve the diffusion capability of a sterilant is only needed in a vacuum exhaust process.

In various sterilization methods using hydrogen peroxide vapor, the aforementioned vacuum exhaust method using the second vacuum pump can continuously maintain the vacuum exhaust performance.

This is because a hydrogen peroxide aqueous solution is needed to use hydrogen peroxide vapor, because a high vacuum level is needed to control the vaporization of hydrogen peroxide since the vapor pressure of hydrogen peroxide vapor is very low, and because the oil of the vacuum pump continues to trap moisture not only due to a highly humid environment, but also due to water vapor fed into the chamber.

If moisture is trapped in the oil of the vacuum pump, the vacuum exhaust performance may deteriorate, the deformation of the oil of the vacuum pump may be accelerated, the vacuum exhaust time may continue to increase, and as a result, the life of the vacuum pump may be shortened.

An experimental example of the invention will hereinafter be described, but the invention is not limited thereto.

Experimental Example

The speed at which a sterilization chamber having an internal volume of 100 L and maintaining a temperature of 50° C. was exhausted by an oil vacuum pump having an exhaust capacity of 600 L per minute was measured.

A check valve and a dry vacuum pump were connected in parallel between the oil vacuum pump and an oil mist trap. In response to a vacuum level in the sterilization chamber reaching 10 mb, the dry vacuum pump was driven. Then, the oil vacuum pump and the dry vacuum pump were driven at the same time until the vacuum level in the sterilization chamber reached 0.1 mb. Once a target vacuum level was reached, the two vacuum pumps were turned off, and the sterilization chamber was purged to atmospheric pressure. At a temperature of 27° C. and at a relative humidity of 50%, the speed at which the sterilization chamber was vacuum-exhausted from atmospheric pressure to 0.1 mb was measured, and then the sterilization chamber was purged, and by repeatedly performing these processes 100 times, the vacuum exhaust speed was measured, and the amount of oil trapped in the oil mist trap was measured.

Comparative Example

The speed at which a sterilization chamber having an internal volume of 100 L and maintaining a temperature of 50° C. was exhausted by an oil vacuum pump having an exhaust capacity of 600 L per minute was measured. At a temperature of 27° C. and at a relative humidity of 50%, the speed at which the sterilization chamber was vacuum-exhausted from atmospheric pressure to 0.1 mb was measured, and then the sterilization chamber was purged, and by repeatedly performing these processes 100 times, the vacuum exhaust speed was measured, and the amount of oil trapped in the oil mist trap was measured.

The results of the experimental example and the comparative example will hereinafter be described.

The results of the experimental example are as follows.

The vacuum exhaust speed was measured to be 252 seconds in the first cycle, 255 seconds in the tenth cycle, and 262 seconds in the hundredth cycle. After the hundredth cycle, the temperature of the oil of the vacuum pump was 45° C. to 50° C., and less than 10 cc of oil was trapped. The vacuum exhaust speed was 253 seconds, as measured in response to the oil of the vacuum pump being returned to room temperature.

The results of the comparative example are as follows.

The vacuum exhaust speed was measured to be 251 seconds in the first cycle, 255 seconds in the tenth cycle, and 361 seconds in the hundredth cycle. After the hundredth cycle, the temperature of the oil of the vacuum pump was 59° C. to 62° C., and less than 80 cc of oil was trapped. The vacuum exhaust speed was 331 seconds, as measured in response to the oil of the vacuum pump being returned to room temperature.

As is apparent from the results of the experimental example and the comparative example, the vacuum exhaust speed of the experimental example, which was measured to be 252 seconds in the first cycle, 255 seconds in the tenth cycle, and 262 seconds in the hundredth cycle, did not much fluctuate from the first cycle to the tenth cycle to the hundredth cycle. On the other hand, the vacuum exhaust speed of the comparative example increased incrementally from 251 seconds in the first cycle to 255 seconds in the tenth cycle to 361 seconds in the hundredth cycle.

In general, the more the water vapor trapped in the oil of an oil vacuum pump, the slower the vacuum exhaust speed becomes.

The experimental example in accordance with the invention produced slight increases in vacuum exhaust speed, but the vacuum exhaust speed in the hundredth cycle was almost similar to the vacuum exhaust speed in the first cycle. On the other hand, in the case of the comparative example, there was a considerable increase in vacuum exhaust speed from the first cycle to the hundredth cycle, which basically means that the vacuum speed considerably decreases as the amount of water vapor trapped in the oil of the oil vacuum pump increases.

The temperature of the vacuum pump oil in the hundredth cycle of the experimental example was 45° C. to 50° C., but the temperature of the vacuum pump oil in the hundredth cycle of the experimental example was 59° C. to 62° C.

Generally, water vapor undergoes an endothermic reaction while being vaporized. The temperature of the vacuum pump oil in the hundredth cycle of the experimental example was measured to be lower than the temperature of the vacuum pump oil in the hundredth cycle of the experimental example, and this means that the water vapor trapped in the oil of the oil vacuum pump had an endothermic reaction in the process of vaporization and thus suppressed an increase in the temperature of the oil of the oil vacuum pump.

That is, it is clear that the amount of vaporization of water vapor was larger in the experimental example than in the comparative example, and that less water vapor was trapped in the oil of the oil vacuum pump in the experimental example than in the comparative example.

Application Example

The effects of the vacuum exhaust system of the sterilizer according to the first exemplary embodiment of FIG. 3 were measured.

A vacuum pump having a capacity of 1000 L per minute was used, and 5.5 cc of 55% hydrogen peroxide was fed into a sterilization chamber having an internal volume of 130 L. Then, the removal of moisture from the hydrogen peroxide was performed during a vacuum exhaust process, and the amount of time taken to vacuum-exhaust the sterilization chamber to a vacuum level of 0.5 mb was measured, which was about 7 minutes.

Thereafter, hydrogen peroxide vapor was diffused into the sterilization chamber and was then maintained for a predetermined amount of time. The amount of time taken to diffuse and maintain the hydrogen peroxide vapor was about 6 minutes.

Thereafter, the sterilization chamber was vacuum-exhausted again to completely purge the hydrogen peroxide vapor and to maintain a vacuum level of 0.5 mb or lower for three minutes. The amount of time taken to vacuum-exhaust the sterilization chamber again was about 6 minutes.

The duration of each cycle, which is defined as two repetitions of the aforementioned processes, was about 40 minutes, the operating time of the oil vacuum pump was 26 minutes, and the operating time of the dry vacuum pump was 22 minutes.

Variations in the duration of each cycle, caused by delays in vacuum exhaust speed, were measured, and the results are as shown in Table 4 below.

TABLE 4

| Amount of time added to standard cycle duration | $100^{th}$ cycle | $500^{th}$ cycle | $1500^{th}$ cycle | $200^{th}$ cycle |
|---|---|---|---|---|
| When driving dry vacuum pump | +0.2 min | +0.3 min | +0.5 min | +1 min |
| When not driving dry vacuum pump | +1.5 min | +7.8 min | *** | *** |

*** Due to failure to reach the target vacuum level, the corresponding cycle could not be terminated properly and thus could not be measured.

Referring to Table 4, the duration of the $100^{th}$ cycle using a dry vacuum pump in accordance with the invention was measured to be 40.2 minutes, which is 0.2 minutes longer than the standard duration of each cycle. On the other hand, the duration of $100^{th}$ cycle not using a dry vacuum pump is 1.5 minutes longer than the standard duration of each cycle.

Also, the duration of the $500^{th}$ cycle using a dry vacuum pump in accordance with the invention and the duration of the $500^{th}$ cycle not using a dry vacuum pump, which are 0.3 minutes and 7.8 minutes, respectively, longer than the standard duration of each cycle, considerably differ from each other.

That is, as mentioned above, the more the water vapor trapped in the oil of an oil vacuum pump, the slower the vacuum exhaust speed becomes. According to the invention, since there is no water vapor trapped in the oil of an oil vacuum pump, there is not much difference in the duration of each cycle that may be caused by delays in vacuum exhaust speed, but when not using a dry vacuum pump, delays in vacuum exhaust speed occur due to water vapor trapped in the oil of an oil vacuum pump.

When not using a dry vacuum pump, water vapor is highly likely to be trapped in the oil of an oil vacuum pump after about 600 times of use of the oil vacuum pump. Thus, the target vacuum level of the oil vacuum pump cannot be reached, and the oil vacuum pump cannot properly serve as a vacuum pump. On the other hand, in the case of using a dry vacuum pump in accordance with the invention, an oil vacuum pump can be used even up to 2000 times.

FIG. 6 is a schematic perspective view of a vacuum exhaust system of a sterilizer according to a second exemplary embodiment of the present disclosure.

The vacuum exhaust system of the sterilizer according to the second exemplary embodiment may be almost similar to the vacuum exhaust system of the sterilizer according to the first exemplary embodiment of FIG. 1, and will hereinafter be described, focusing mainly on differences with the first exemplary embodiment.

Referring to FIG. 6, the vacuum exhaust system of the sterilizer according to the second exemplary embodiment includes a heat exchanger 70, which is for cooling a first vacuum pump 20.

As is clear from the aforementioned application example, in the case of using a first vacuum pump in a sterilization process, the first vacuum pump is generally driven for a long time, and thus, the operating oil of the first vacuum pump is heated so that the viscosity of the first vacuum pump decreases. As a result, the first vacuum pump is degraded, and thus, the life of the first vacuum pump is shortened.

Accordingly, according to the invention, the operating oil of the first vacuum pump may preferably be cooled to be prevented from being heated, and the operating oil of the first vacuum pump may be cooled by the heat exchanger 70.

As illustrated in FIG. 6, the vacuum exhaust system of the sterilizer according to the second exemplary embodiment may also include an operating oil circulating pump 60, which is for circulating the operating oil of the first vacuum pump. That is, the operating oil is circulated by the operating oil circulating pump 60, and may be cooled by the heat exchanger 70 while being circulated.

The phrase "the operating oil is circulated", as used herein, means that the operating oil is released from the first vacuum pump and is fed back into the first vacuum pump through the heat exchanger, as illustrated in FIG. 6.

Thus, according to the invention, the operating oil of the first vacuum pump is cooled by the heat exchanger while being circulated. Thus, it is possible to prevent the operating oil of the first vacuum pump from being heated and thus to prevent the viscosity of the operating oil of the first vacuum pump from being lowered or the operating oil of the first vacuum pump from being degraded.

FIG. 7 is a schematic view of a vacuum exhaust system of a sterilizer according to a third exemplary embodiment of the present disclosure.

The vacuum exhaust system of the sterilizer according to the third exemplary embodiment may be almost similar to the vacuum exhaust system of the sterilizer according to the first exemplary embodiment of FIG. 1.

Referring to FIG. 7, the vacuum exhaust system of the sterilizer according to the third exemplary embodiment includes a sterilization chamber 310.

The vacuum exhaust system of the sterilizer according to the third exemplary embodiment may also include a sterilant solution feeding device 340, and a target object to be sterilized may be sterilized in the sterilization chamber 310 with a sterilant fed by the sterilant solution feeding device 340.

A sterilant solution feeding control valve 341 may be provided between the sterilant solution feeding device 340 and the sterilization chamber 310 and may feed an appropriate amount of sterilant solution.

The vacuum exhaust system of the sterilizer according to the third exemplary embodiment may also include a first vacuum pump 320, which is connected to the other side of the sterilization chamber 310, and the first vacuum pump 320 may create a vacuum by pumping the gas out of the sterilization chamber 310.

The first vacuum pump 320 may be an oil vacuum pump.

A first vacuum valve 321, which is capable of controlling the operation of the first vacuum pump 320, may be connected between the sterilization chamber 310 and the first vacuum pump 320. A catalyst reaction section 322 may also be provided between the sterilization chamber 310 and the first vacuum pump 320.

Referring further to FIG. 7, the vacuum exhaust system of the sterilizer according to the third exemplary embodiment may also include an oil mist trap section 350.

The oil mist trap section 350 is a part for trapping an oil from vapor introduced from the sterilization chamber 310 and released via the first vacuum pump 320. An oil may be trapped by the oil mist trap section 350, and vapor may be discharged through the oil mist trap section 50.

Referring further to FIG. 7, the vacuum exhaust system of the sterilizer according to the third exemplary embodiment may also include a second vacuum pump 330, which is connected between the first vacuum pump 320 and the oil mist trap section 350.

The second vacuum pump 330 may be a dry vacuum pump not using an oil.

The second vacuum pump 330 is configured to expose an operating oil of the first vacuum pump 320 to a vacuum level with a predetermined pressure, and the predetermined pressure may be a pressure at which moisture trapped in the operating oil can reach a point below its boiling point.

The functions of the second vacuum pump 330 are as described above with regard to the first exemplary embodiment, and thus, a detailed description thereof will be omitted.

It will hereinafter be described how the second vacuum pump 330 is connected to the first vacuum pump 320 and the oil mist trap section 350.

Referring to FIG. 7, the second vacuum pump 330 may be connected in series to the first vacuum pump 320 and the oil mist trap section 350.

A first path opening/closing valve section 332 is provided between the first vacuum pump 320 and the oil mist trap section 350. The first path opening/closing valve section 332 may be a check valve.

The second vacuum pump 330 and the first path opening/closing valve section 332 are connected in parallel between the first vacuum pump 320 and the oil mist trap section 350.

That is, in the third exemplary embodiment, a first path including the first vacuum pump 320, the first path opening/closing valve section 332, and the oil mist trap section 350 may be controlled by the first path opening/closing valve section 332, and a second path including the first vacuum pump 320, the second vacuum pump 330, and the oil mist trap section 350 may be controlled by the second vacuum pump 330.

In general, a vacuum pump may perform the functions of a valve. Thus, even if no particular opening/closing valve section is provided between the first and second vacuum pumps, as illustrated in FIG. 1, water vapor introduced from the first vacuum pump 330 may be allowed by the first vacuum pump 330 to pass through the oil mist trap section 350 via the second vacuum pump 330.

As mentioned above, the first path opening/closing valve section 332 may preferably be a check valve. The check valve may be opened or closed by pressure applied thereto, rather than by an electric signal.

That is, in response to a predetermined pressure being applied to the check valve, the check valve may be opened due to a mechanical mechanism, in which case, water vapor introduced from the first vacuum pump 330 may be allowed to pass through the oil mist trap section 350 via the check valve 332.

In other words, in the first exemplary embodiment, two valve sections are used to control two paths, as described above with reference to FIG. 1. On the other hand, in the third exemplary embodiment, the first path including the first vacuum pump 320, the first path opening/closing valve section 332 and the oil mist trap section 350 may be controlled by the first path opening/closing valve section 332, and the second path including the first vacuum pump 320, the second vacuum pump 330, and the oil mist trap section 350 may be controlled by the second vacuum pump 330.

A vacuum exhaust method of the vacuum exhaust system of the sterilizer according to the third exemplary embodiment will hereinafter be described. The vacuum exhaust method of the vacuum exhaust system of the sterilizer according to the third exemplary embodiment may be almost similar to the vacuum exhaust method of the vacuum exhaust system of the sterilizer according to the first exemplary embodiment except for the following.

The vacuum exhaust method of the vacuum exhaust system of the sterilizer according to the third exemplary embodiment includes vacuum-exhausting the vacuum chamber by turning on the first vacuum pump 320 (S311).

In S311, the first vacuum valve 321 may be open, the second vacuum pump 330 may be off, and the first path opening/closing valve section 332, i.e., a check valve, may be open due to a difference in pressure.

Thereafter, by turning on the second vacuum pump 330, a vacuum may be applied to the operating oil of the first vacuum pump (S312).

As mentioned above, some of water vapor passing through the first vacuum pump either continues to evaporate or is dissolved and released into the air. However, the water vapor cannot be completely discharged, and some of the water vapor may be trapped and accumulated in the oil of the vacuum pump in the form of a liquid.

Thus, according to the invention, a predetermined pressure may be provided to allow the water in a liquid state in the oil of the first vacuum pump 320 to evaporate, and the second vacuum pump 330 may provide a predetermined pressure for vaporizing the water in a liquid state trapped in the oil of the first vacuum pump 320.

In S312, the first vacuum valve 321 may be open, the second vacuum pump 330 may be on, and the first path opening/closing valve section 332 may be closed.

Thereafter, water vapor trapped in the operating oil of the first vacuum pump is vaporized (S313).

S312 and S313 may be performed at the same time. That is, the predetermined pressure for vaporizing the water in a liquid state in the first vacuum pump may be provided to the first vacuum pump 320 by turning on the second vacuum pump so as to apply a vacuum to the operating oil of the first vacuum pump, and as a result, water vapor trapped in the operating oil of the first vacuum pump may be vaporized. S313 is the same as its counterpart of the first exemplary embodiment, and thus, a detailed description thereof will be omitted.

In S313, the first vacuum valve 321 may be open, the second vacuum pump 330 may be on, and the first path opening/closing valve section 332 may be closed.

Thereafter, the first vacuum pump is turned off, and the second vacuum pump is maintained to be turned on (S314).

That is, in S314, the first vacuum pump may be turned off to terminate the vacuum-exhausting of the sterilization chamber, but the water in a liquid state trapped in the operating oil of the first vacuum pump may continue to be vaporized.

In S314, the first vacuum valve 321 may be closed, the second vacuum pump 330 may be on, and the first path opening/closing valve section 332 may be closed.

Thereafter, by turning off the second vacuum pump, the vacuum exhaust process of the vacuum exhaust system of the sterilizer according to the third exemplary embodiment is completed.

The exemplary embodiments of the invention have been described with reference to the accompanying drawings. However, those skilled in the art will appreciate that many variations and modifications can be made to the disclosed embodiments without substantially departing from the principles of the invention. Therefore, the disclosed embodiments of the invention are used in a generic and descriptive sense only and not for purposes of limitation.

What is claimed is:

1. A vacuum exhaust method of a sterilizer, comprising:
   exhausting a vacuum chamber by turning on a first vacuum pump;
   applying a vacuum to an operating oil of the first vacuum pump by turning on a second vacuum pump; and
   vaporizing water vapor trapped in the operating oil of the first vacuum pump.

2. The vacuum exhaust method of claim 1, further comprising, after the vaporizing the water vapor:
   turning off the first vacuum pump and maintaining the second vacuum pump to be turned on; and
   turning off the second vacuum pump.

3. The vacuum exhaust method of claim 1, further comprising, after the vaporizing the water vapor:
   turning off the second vacuum pump.

4. The vacuum exhaust method of claim 1, further comprising, after the exhausting the vacuum chamber:
   terminating the exhausting of the vacuum chamber by turning off the first vacuum pump.

* * * * *